United States Patent [19]

Daren et al.

[11] Patent Number: 4,748,286

[45] Date of Patent: May 31, 1988

[54] PRODUCTION OF CRYSTALLINE TRIBROMOSTYRENE

[75] Inventors: Stephen L. J. Daren, Ness Ziona; David Vofsi, Haifa; Aurelia Finkels, Rehovot, all of Israel

[73] Assignee: Yeda Research & Development Co. Ltd., Rehovot, Israel

[21] Appl. No.: 78,004

[22] Filed: Jul. 21, 1987

[30] Foreign Application Priority Data

Jul. 23, 1986 [IL] Israel .................................. 79499

[51] Int. Cl.$^4$ ...................... C07C 17/34; C07C 17/38; C07C 17/24
[52] U.S. Cl. .................................. 570/200; 570/204; 570/211
[58] Field of Search ................ 570/193, 204, 200, 211

[56] References Cited

U.S. PATENT DOCUMENTS

| | | | |
|---|---|---|---|
| 3,966,831 | 6/1976 | Levy et al. | 570/200 |
| 3,980,722 | 9/1976 | Cohen et al. | 570/200 |
| 4,292,453 | 9/1981 | Daren et al. | 570/193 |
| 4,423,262 | 12/1983 | Jackisch | 570/193 |
| 4,633,026 | 12/1986 | Kolich | 570/193 |
| 4,686,311 | 8/1987 | Jackisch | 570/193 |

Primary Examiner—J. E. Evans
Attorney, Agent, or Firm—Browdy & Neimark

[57] ABSTRACT

The invention relates to an improved process for the production of crystalline tribromostyrene. The process involves removal of hydrogen bromide in a two phase system with the aid of phase transfer catalysts. One of the phases used is an aqueous one containing an alkali metal hydroxide whereas the second comprises β-bromoethyltribromobenzene in an alcohol as solvent.

6 Claims, No Drawings

PRODUCTION OF CRYSTALLINE TRIBROMOSTYRENE

FIELD OF THE INVENTION

It is an object of the invention to provide an improved method for the production of crystalline tribromostyrene.

PRIOR ART

U.S. Pat. No. 4,292,453, relates to the production of tribromostyrene using methylene chloride as solvent. U.S. Pat. No. 4,423,262 relates to the production of dibromostyrene using t-BuOH. According to the former, tribromostyrene is not isolated from the reaction mixture in a crystalline form, and remains in a solution of $CH_2Cl_2$. Its ultimate isolation from such solution results in poor yields. Another drawback is in the use of excess alkali (a ratio of NaOH to substrate of 5:1) and long reaction times—10 hours.

SUMMARY OF THE INVENTION

The invention relates to a process for the production of crystalline tribromostyrene which comprises effecting an elimination of hydrogen bromide in a two-phase system by phase transfer catalysis, said phases comprising an aqueous phase of an alkali metal hydroxide and a second phase comprising the β-bromoethyltribromobenzene substrate in a solvent selected from $C_1$- to $C_3$-alchohols. A preferred embodiment relates to a process where β-bromoethyltribromobenzene, triethylbutyl ammonium bromide, sodium nitrite and isopropanol are stirred with aqueous sodium hydroxide so as not to exceed about 40° C., filtering off the resulting tribromostyrene, dissolving in a suitable solvent, washing, drying and removing part of the solvent under reduced pressure, and cooling to obtain the crystalline product.

When using a two-phase system for the elimination reaction of the hydrogen bromide from the substrate β-bromoethyltribromobenzene by phase transfer catalysis, there exist two phases consisting of aqueous NaOH on the one hand, and a mixture of the substrate in an alcohol chosen from among the series of $C_1$–$C_3$ alcohols on the other. Tribromostyrene formed in the reaction separates in crystalline form at the reaction temperature in substantially pure form. This does not happen in "good" solvents such as $CH_2Cl_2$ or certain "poor" solvents such as t-BuOH.

It is surprising that only the $C_1$ to $C_3$ alcohols, when used as solvents for the substrate, provide such a selective process.

PROCEDURE

The reaction is carried out in a preferred mode, by taking a molar ratio of NaOH (45% aqueous solution) to substrate of about 2.5:1. The organic phase consists of a solution of β-bromoethyltribromobenzene in the appropriate alcohol, the preferred one being isopropanol. The catalytic system is a quaternary ammonium salt plus sodium nitrite as in U.S. Pat. No. 4,292,453. The reaction mixture is strongly stirred and is kept at 35°–40° C. for a total of 45 minutes.

EXAMPLES

In U.S. Pat. No. 4,292,453, Example No. 5 describes the synthesis of tribromostyrene using methylene chloride as a solvent. The conditions described require a molar ratio of caustic to β-bromoethyltribromobenzene of 5:1 and 10 hours reaction time at 30° C.

The process of the invention using a select solvent for the reaction, results in a much shorter reaction time with a considerably reduced amount of caustic.

The starting material for the reactions described was obtained by brominating β-bromoethylbenzene with three moles of bromine at 40° C. in the dark and in the presence of 0.5% by wt of reduced iron catalyst. The gas chromatographic composition of the starting material was as follows:

beta-bromoethyldibromobenzene=5%
beta-bromoethyl-2,4,5-tribromobenzene=82%
beta-bromoethyl-2,4,6-tribromobenzene=8%
beta-bromoethyltetrabromobenzene=5%

The overall concentration of the above components was 97% with 3% of unidentified heavy products.

EXAMPLE 1

105.5 g β-bromoethyl tribromobenzene (as above) (0.25 mol), 1 g triethylbutyl ammonium bromide (as 50% aq.solution) 50 g isopropyl alcohol and 1 g sodium nitrite were stirred at about 500 rpm. in a 1 liter three-necked flask at room temperature. 55.6 g 45% NaOH solution (0.625 mol) were added slowly such that the reaction exotherm gradually raised the temperature to 35° C. When necessary an ice-water bath was raised under the flask to control the temperature. After about 5 minutes of reaction, tribromostyrene started to precipitate from the solution. The stirring was continued for a total of 45 mins. At the end of this period the reaction mixture was filtered using a water vacuum pump. The solid remaining in the funnel was tribromostyrene. The filtered liquid consisted of three separate phases—an aqueous mixture of sodium bromide and hydroxide, an isopropanol phase and a small dark layer containing the heavies. The tribromostyrene was dissolved in n-hexane (approx 150 g), washed with dilute HCl and water and dried over calcium chloride. After filtering off the calcium chloride, the hexane was removed under vacuum at 40° C. until the first crystals appeared. The hexane solution was allowed to cool slowly to room temperature and then in an ice-water bath. The crystals were filtered off, and dried overnight in a vacuum oven at 40° C. 62 g 2,4,5-tribromostyrene were obtained (m.p=64° C.). In the mother liquor (hexane) were dissolved approx. 12 g of products consisting of a mixture of tribromo and tetrabromostyrenes. The isopropanol phase contained about 8 g of product mixtures including dibromostyrene.

EXAMPLE 2 (COMPARATIVE EXAMPLE)

A run was carried out as in Example 1, but without isopropanol. A mixture of heavy liquids was obtained, but no crystalline tribromostyrene could be isolated.

EXAMPLE 3 (COMPARATIVE EXAMPLE)

A run was carried out as in Example 1, but with methylene chloride instead of isopropanol. At the end of the reaction the methylene chloride was evaporated under vacuum, the product dissolved in hexane and worked up as described above. 64 g of a viscous liquid were obtained. No tribromostyrene could be isolated by crystallization.

EXAMPLE 4

A run was carried out as in Example 1, but with ethanol instead of isopropanol. 61 g tribromostyrene were obtained (m.p. 55° C.). As indicated by the depressed m.p. an additional crystallization was required to obtain a product of m.p. 64° C.

EXAMPLE 5 (COMPARATIVE EXAMPLE)

A run was carried out as in Example 1, but with t-butanol instead of isopropanol. An inseperable mass was obtained at the end of the reaction.

EXAMPLE 6

A run was carried out as in Example 1, but with 200 g methanol instead of isopropanol. 72 g, tribromostyrene were obtained after crystallization (m.p.=60° C.).

We claim:

1. A process for the production of crystalline tribromostyrene which comprises effecting an elimination of hydrogen bromide in a two-phase system by phase transfer catalysis, said phases comprising an aqueous phase of an alkali metal hydroxide and a second phase comprising the β-bromoethyltribromobenzene substrate in a solvent selected from $C_1$- to $C_3$- alcohols.

2. A process according to claim 1, where β-bromoethyltribromobenzene, triethylbutyl ammonium bromide, sodium nitrite and isopropanol are stirred with aqueous sodium hydroxide so as not to exceed about 40° C., filtering off the resulting tribromostyrene, dissolving in a suitable solvent, washing, drying and removing part of the solvent under reduced pressure, and cooling to obtain the crystalline product.

3. A process according to claim 1, where the alcohol used is methanol.

4. A process according to claim 1, where the alcohol used in ethanol.

5. A process according to claim 1, where the solvent is isopropanol.

6. A process according to claim 1, where the ratio of alkali metal hydroxide to substrate is from 2:1 and up to 4:1.

* * * * *